United States Patent [19]
Rogers

[11] Patent Number: 5,848,894
[45] Date of Patent: Dec. 15, 1998

[54] DELIVERY SYSTEM FOR NON-AQUEOUS PASTE DENTAL MATERIALS

[75] Inventor: Ralph F. Rogers, Woodbury, Minn.

[73] Assignee: Minnesota Mining and Manufacturing Company, St. Paul, Minn.

[21] Appl. No.: 672,253

[22] Filed: Jun. 28, 1996

[51] Int. Cl.⁶ .................................................. A61C 5/04
[52] U.S. Cl. ............................................................ 433/90
[58] Field of Search ............................................ 433/90

[56] References Cited

U.S. PATENT DOCUMENTS

| | | | |
|---|---|---|---|
| 2,903,794 | 9/1959 | Carfagni | 433/90 |
| 3,581,399 | 6/1971 | Dragan | 32/60 |
| 3,595,439 | 7/1971 | Newby | 222/80 |
| 3,900,954 | 8/1975 | Dragan | 32/60 |
| 4,084,320 | 4/1978 | Skeirik | 433/90 |
| 4,391,590 | 7/1983 | Dougherty | 433/90 |
| 4,538,920 | 9/1985 | Drake | 366/177 |
| 4,551,135 | 11/1985 | Gorman | 433/90 |
| 4,552,266 | 11/1985 | Weissenburger | 206/63.5 |
| 4,664,257 | 5/1987 | Wilson | 206/63.5 |
| 4,767,326 | 8/1988 | Bennett | 433/90 |
| 4,798,596 | 1/1989 | Muhlbauer | 433/90 |
| 5,100,320 | 3/1992 | Martin | 433/90 |
| 5,171,149 | 12/1992 | Alpert | 433/217.1 |
| 5,401,169 | 3/1995 | Fleisher | 433/90 |
| 5,501,727 | 3/1996 | Wang | 106/35 |
| 5,554,665 | 9/1996 | Tateosian et al. | 433/90 X |
| 5,624,260 | 4/1997 | Wilcox et al. | 433/90 |

FOREIGN PATENT DOCUMENTS

| | | | |
|---|---|---|---|
| 2260515 | 9/1975 | France | 433/90 |
| 56-0151036 | 11/1981 | Japan | 206/63.5 |

OTHER PUBLICATIONS

"Modern Plastics Encyclopedia", vol. 65, No. 11, pp. 148–150, McGraw–Hill, New York (1988).

Primary Examiner—Jeffrey A. Smith
Attorney, Agent, or Firm—Dale A. Bjorkman

[57] ABSTRACT

A cartridge for delivery of non-aqueous paste dental materials is provided, wherein the cartridge comprises a cartridge body made from an injection moldable material comprising amorphous polyolefin polymers. The cartridge contains only non-aqueous materials.

16 Claims, 4 Drawing Sheets

DELIVERY SYSTEM FOR NON-AQUEOUS PASTE DENTAL MATERIALS

FIELD OF THE INVENTION

The present invention relates to delivery systems for non-aqueous paste dental materials. More particularly, this invention relates to cartridge bodies for delivery of non-aqueous paste dental materials using hand-held ejector-type dispensers.

BACKGROUND OF THE INVENTION

Hand-held ejector-type dispensing systems have long been used for delivery of multiple-part silicone dental impression materials. The standard in the industry has heretofore been the use of polypropylene as the material of choice for manufacture of the cartridge body, together with silicone O-rings on the plunger for applying force to extrude the material from the cartridge body. Devices useful for delivery of such materials include multiple barrel dispensing devices having a static mixer provided to efficiently mix the separate components as they are extruded from the barrels of the device. An example of such a device is described in U.S. Pat. No. 4,538,920 to Drake.

U.S. Pat. No. 5,100,320 discloses a cartridge for delivery of dental compositions. The material from which the cartridge is manufactured must have a burst value greater than that of an otherwise identical cartridge made entirely of polypropylene and a 24 hour water absorption less than nylon-6. These materials are discussed at column 4, lines 3–12.

SUMMARY OF THE INVENTION

The present invention provides a cartridge for delivery of polymerizable non-aqueous paste dental materials, said cartridge comprising a) a cartridge body made from an injection moldable material comprising a polymer selected from the group consisting of polyolefin polymers and b) a polymerizable non-aqueous paste dental material contained within at least one of the separate chambers of the cartridge body. The cartridge has a 24 Hour Water Absorption of less than 0.3%, a Burst Value of at least 30 kg, and an Oxygen Permeability greater than 180 $cm^3$ mil/$m^2$ day atm.

The cartridge body comprises at least one chamber adapted for holding a non-aqueous paste dental material and simultaneously dispensing same. The polymerizable non-aqueous paste dental material contained within the chamber of the cartridge body comprises a volatile organic diluent. The cartridge is specially adapted to be mounted in a hand-held ejector-type gun, and the cartridge contains only non-aqueous materials.

BRIEF DESCRIPTION OF DRAWING

A preferred embodiment of the invention is illustrated in the accompanying drawing, in which.

DETAILED DESCRIPTION OF PRESENTLY PREFERRED EMBODIMENTS

Non-aqueous pastes comprising volatile organic material may be subject to storage problems wherein the consistency of the material becomes unacceptable over time. It has surprisingly been found that non-aqueous dental materials are very sensitive to loss of volatile organic diluent, and to change in the amount of trace water that may be present in the system. If during storage, the volatile components are lost, or trace water is added to or removed from the paste, consistency problems can occur.

Conventional cartridge materials utilized in the dental industry tend to absorb water. This has been found to be a problem even for non-aqueous paste materials, because the moisture content of the paste over time will depend on the amount of water residing in the capsule at the time of manufacture and if allowed to be exposed to humid conditions. If the capsule is dry, it will act as a dessicant with respect to any hydrated species in the paste and therefore change the consistency of the paste. If the capsule contains much water, the capsule will act as a water source for the paste, adding unwanted water to the system.

In addition to providing low water absorption for consistency stability, the cartridge must also allow permeation of oxygen to provide polymerization stability. When oxygen fails to penetrate to the polymerizable paste, a reaction starts at the core of the sample, and progresses out to the edges until the entire sample is polymerized.

The capsule additionally must have a high Burst Value, i.e. the capsule must not burst when attempting to extrude material from it.

The cartridge body is made from an injection moldable material comprising a polymer selected from the group consisting of amorphous polyolefin polymers. The injection moldable material has a 24 Hour Water Absorption of no more than about 0.3%, more preferably no more than about 0.2%, and most preferably no more than about 0.1%. The injection moldable material has an Oxygen Permeability greater than about 180 $cm^3$ mil/$m^2$ day atm. Preferably, the injection moldable material has an Oxygen Permeability greater than about 350 $cm^3$ mil/$m^2$ day atm., and more preferably greater than about 700 $cm^3$ mil/$m^2$ day atm. The cartidge made from the injection moldable material has a Burst Value of greater than about 30 kg, more preferable greater than about 40 kg, and most preferably greater than about 50 kg. Test methodologies for determining these physical characteristics are set forth in the Examples below.

Examples of suitable amorphous polyolefin materials useful as a primary component of the injection moldable material include polyethylene, polypropylene, polybutylene and the like. The polymers may be homopolymers or copolymers with other suitable repeating units, either as random or block copolymers. Optionally, the polymer may be selected from linear, branched, crosslinked, uncrosslinked, fluorinated, hydrogenated or partially hydrogenated olefin polymers. The polymer may also be prepared from a ring-strained cyclic olefin. These polymers may additionally be blended with compatible additional polymers, so long as the material as a whole is injection moldable and has the physical property characteristics required. The cartridge is preferably integrally molded of an amorphous polyolefin such as is sold under the trade name "ZEONEX" (from Nippon Zeon Co., Ltd., Tokyo, Japan).

The injection moldable material may also optionally comprise a reinforcing filler. Suitable reinforcing fillers include carbon fiber, mica, calcium carbonate, talc, polytetrafluoroethylene, glass (e.g., chopped glass, continuous glass fiber), aluminum flake, mixtures thereof, and the like.

The particular amount of a reinforcing filler that can be used with a material varies from filler to filler and from material to material. Therefore, it is impractical to recite a particular range of filler levels suitable to all fillers and all polymeric materials. In general, however, a filled material can comprise about 10 percent to about 60 percent, preferably 20 percent to about 50 percent, by weight reinforcing filler based on the total weight of the filled material.

Transparent injection moldable materials can be made opaque by coating (e.g., painting or covering with a label) or preferably by incorporating pigments such as titanium dioxide and carbon black, or colorants (e.g., pigments and/or dyes) in order to prevent actinic light from reaching the dental composition contained therein. Colorants can be incorporated into the injection moldable material according to well known methods, e.g., as disclosed in the *Modern Plastics Encyclopedia*, Vol. 65, No. 11, pp. 148–150, McGraw-Hill New York (1988).

A cartridge of the invention is preferably relatively small, and is intended to contain an amount of a dental composition that can be substantially fully expended during the course of a single procedure or several (e.g., 2 to about 10) procedures. A preferred design for a two-part composition delivery system is disclosed in pending U.S. patent application Ser. No. 08/547451 (now U.S. Pat. No. 5,722,829), filed on Oct. 24, 1995 entitled "DUAL CHAMBER CARTRIDGE DISPENSING SYSTEM FOR DENTAL MATERIAL," the disclosure of which is expressly incorporated by reference hereto.

Wall thickness is such that the cartridge will withstand the pressures exerted during extrusion of a dental composition at a useful rate without bursting or excessive yielding. Preferred wall thickness will vary based on several factors, such as the viscosity of the dental composition, the tensile strength of the material from which a cartridge is made, the dimensions of the inner chamber (e.g., length, shape, and cross-sectional area), and the size of the orifice in the discharge nipple. A particularly preferred thickness is about 1100 to 1300 $\mu$m.

All non-cartridge body components of the cartridge of the present invention preferably possess at least water absorption characteristics, and preferably oxygen permeability characteristics, similar to the cartridge body itself. Thus, the piston also preferably is constructed from a material having a 24 hour water absorption less than 0.3%. Preferably, the piston material has a 24 hour water absorption value of less than 0.2% and more preferably less than 0.1%. While not essential, it is preferred that the piston material have an Oxygen Permeability greater than 180 $cm^3$ mil/$m^2$ day atm. More preferably, the piston material has an Oxygen Permeability greater than 350 $cm^3$ mil/$m^2$ day atm., and most preferably greater than 700 $cm^3$ mil/$m^2$ day atm.

For purposes of the present invention, the term "non-aqueous" means that the composition is substantially free of added water, or that the composition does not contain water that is intentionally added as a non-complexed or coordinated entity. It is understood that many materials, such as metals, inorganic fillers or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect of the long term properties on the composition.

The non-aqueous paste dental materials to be delivered from the cartridge as described above are typically polymerizable dental restorative materials as is well known in the art. These restorative materials typically comprise a mixture of polymerizable monomers and oligomers, and an inorganic filler material. To achieve the appropriate viscosity, the paste comprises one or more volatile diluents and components. Examples of some particularly preferred volatile components that may be provided in the paste are hydroxyethyl methacrylate ("HEMA") and ethylene glycol dimethacrylate, triethylene glycol dimethacrylate ("TEGDMA"), tetraethylene glycol dimethacrylate, polyethylene glycol (200) dimethacrylate, polyethylene glycol (400) diacrylate, polyethylene glycol (400) dimethacrylate, and diethylene glycol diacrylate. The above examples are representative of free radically cured systems. It is understood that the paste may utilize a different polymerization modes, such as a cationic cure mechanism. Examples of cationic cure materials include epoxy materials, oxetanes, oxolanes, cyclic acetals, lactams, lactones, and vinyl ethers or spirocyclic compounds containing O atoms in the rings.

The paste is preferably provided having a consistency after extrusion from the cartridge of about 29 mm to 37 mm, more preferably about 31 mm to 36 mm, and most preferably about 33 mm to 35 mm.

DETAILED DESCRIPTION OF THE DRAWING

Figure 1:
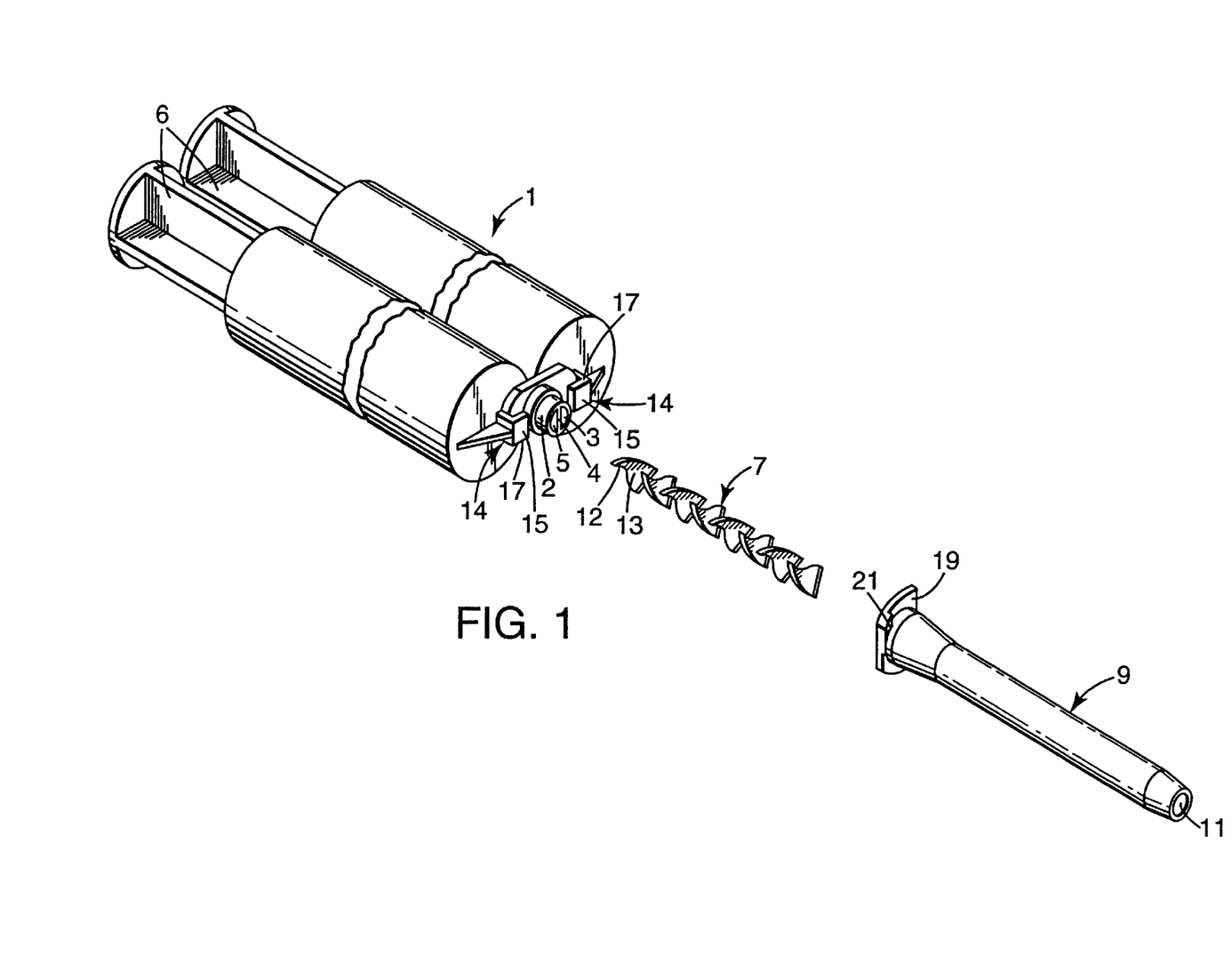
FIG. 1 is an exploded view in perspective of a syringe, static mixing element and exit conduit of this invention.

Referring now to FIG. 1, there is shown an exploded view in perspective of a cartridge of this invention having a static mixing device located thereon. Syringe 1 has two parallel internal chambers, each of which is intended to be filled with one part of a two-part dental paste material. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will react following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

Maximum efficiency of mixing is obtained by ensuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

Figure 2:
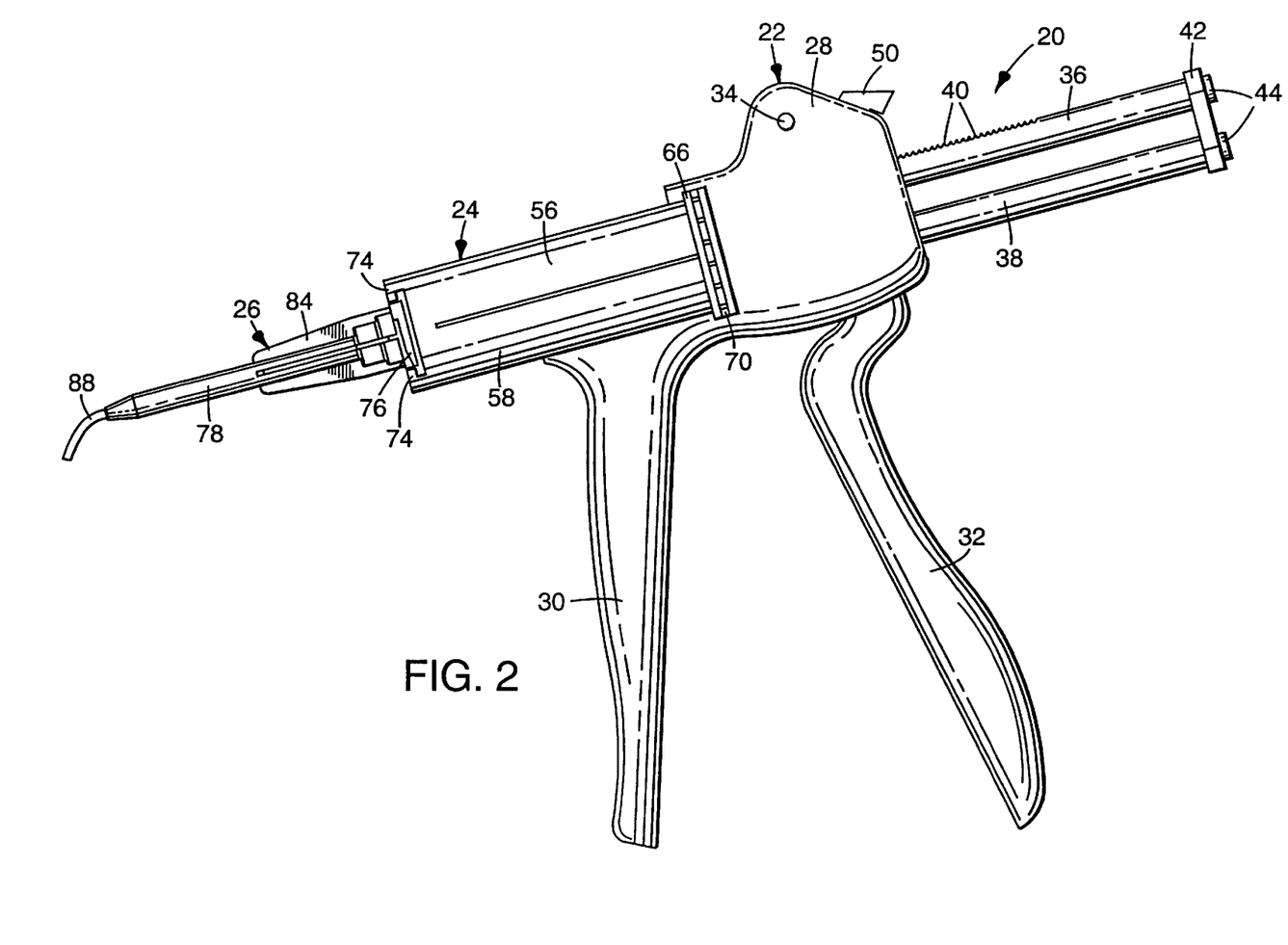
FIG. 2 is a side elevational view of a dispensing system incorporating a cartridge according to the present invention.
Figure 3:
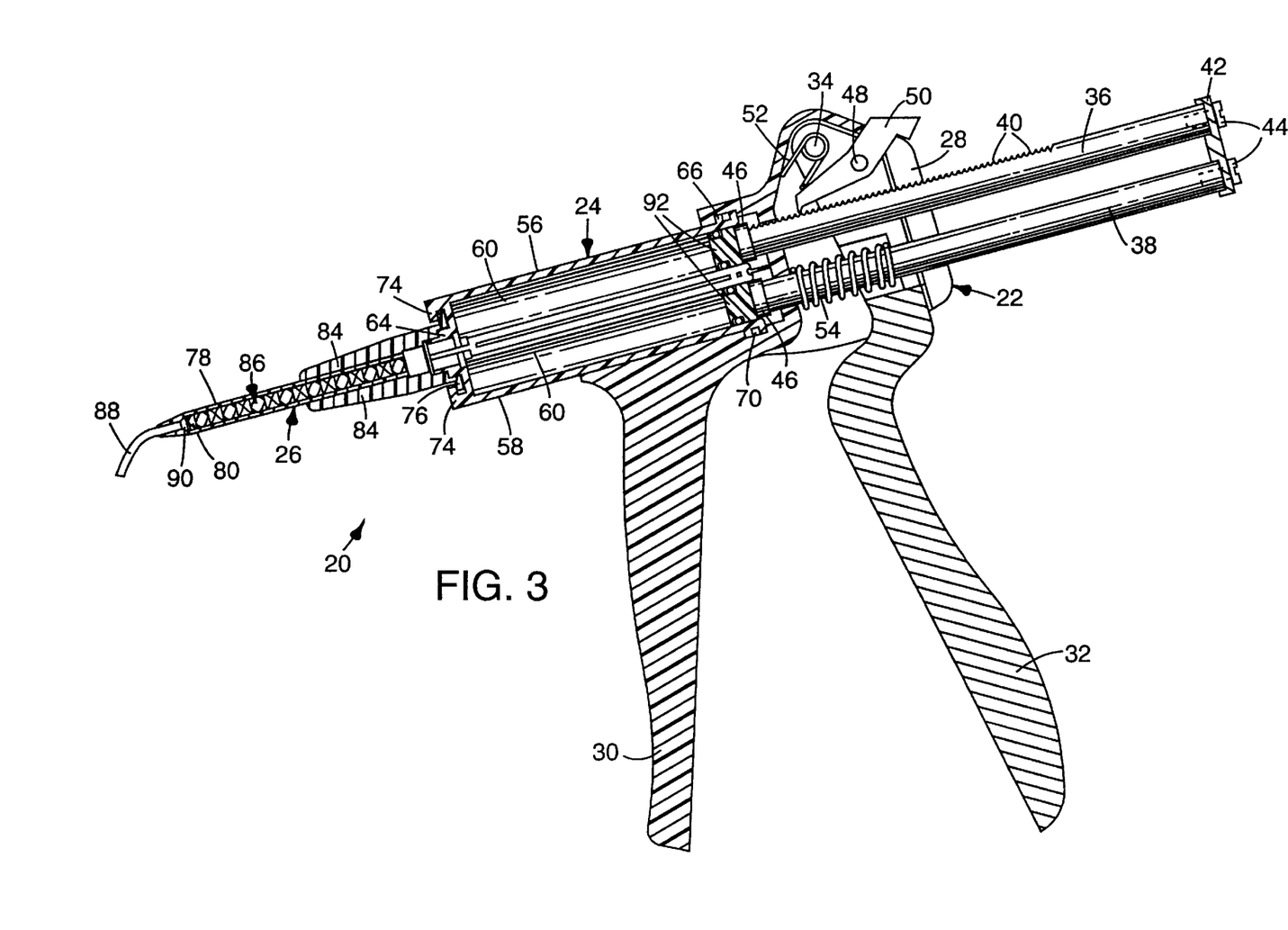
FIG. 3 is a side cross-sectional view of the system shown in FIG. 2.

A dispensing system incorporating a cartridge according to the invention is shown in FIGS. 2–3, and is designated by the numeral 20. The dispensing system 20 broadly includes an applicator 22, a dual chamber dispensing cartridge 24 detachably connected to the applicator 22 and a static mixing assembly 26 that is detachably connected to the front of the cartridge 24.

Turning initially to the applicator 22 in more, detail, the applicator 22 includes a hollow body 28 and an elongated, depending handle 30 that is connected to the body 28. The body 28 and the handle 30 are each made in right and left half-sections that are substantially mirror-image of each other, and in each half-section the corresponding portion of the body 28 is integrally molded with the corresponding portion of the handle 30.

The applicator 22 also includes an arm 32 that depends from the body 28 and is located next to the handle 30. An upper portion of the arm 32 is bifurcated and extends within the hollow area of the body 28. A pivot 34, in the form of a cylindrical metal rod, extends transversely between right and left half-sections of the body 28, and pivotally connects the upper bifurcated portion of the arm 32 to the body 28 to thereby enable the arm 32 to move in swinging fashion relative to the handle 30.

The applicator 22 also includes a first elongated plunger 36 and a second elongated plunger 38 that is located below the first plunger 36 in parallel, side-by-side relation. The handle 30 extends at an angle of preferably less than 90 degrees, and more preferably at an angle of about 75 degrees relative to the longitudinal axes of the plungers 36, 38. Both of the plungers 36, 38 have a smooth cylindrical outer surface, except that the top plunger 36 has a top surface with a series of flat teeth 40 that extend along a major extent of the length of the first plunger 36.

The plungers 36, 38 are secured together for simultaneous movement by a rigid block 42 that is connected to the rear end of the plungers 36, 38 by screws 44. The front end of each plunger 36, 38 includes a slightly enlarged cylindrical head 46 (FIG. 3) that is optionally connected to the corresponding plunger 36, 38 by a longitudinally extending screw (not shown in the drawings).

The plungers 36, 38 pass through two respective holes located in a rear wall of the body 28 and also two respective holes located in an interior wall of the body 28 immediately behind the position of the heads 46 that is illustrated in FIG. 3. The enlarged heads 46, being larger than the adjacent holes in the body 28, prevent the plungers 36, 38 from detaching from the body 28 when the plungers 36, 38 are pulled in a rearward direction. Alternatively, the heads 46 could be eliminated, or be made equal in diameter to the plungers 36, 38 so that the latter could be removed from the body 28 if desired.

A second pivot 48, also in the form of a cylindrical metal rod, extends between the bifurcated sections of the upper portion of the arm 32 immediately behind and somewhat below the pivot 34 as shown in FIG. 2. The pivot 48 passes through a hole in a pawl 50 that extends through the space between the bifurcated upper portion of the arm 32. A coil spring 52 is wrapped around the pivot 34 and has an upper leg that bears upwardly against an upper wall of the body 28 and a lower leg that bears downwardly against a forward section of the pawl 50. The spring 52 urges a chisel-shaped lower front edge of the pawl 50 into releasable engagement with one of the teeth 40 of the upper plunger 36.

A coiled compression spring 54 is also located in the hollow area of the body 28. Advantageously, the spring 54 is received around a portion of the lower plunger 38 in order to save space and obviate the need for additional connecting members or the like. The front end of the spring 54 bears against the inner wall of the body 28, while the rear end of the spring 54 bears against a rear end of a slightly enlarged channel constructed in the opposing sections of the upper bifurcated portion of the arm 32 next to the lower plunger 38. The spring 54 urges the arm 32 in a rearward direction and away from the handle 30.

To advance the plungers 36, 38, the arm 32 is swung about pivot 34. As the arm 32 moves toward the handle 30, engagement of the chisel-shaped lower front edge of the pawl 50 with the teeth 40 causes the plungers 36, 38 to simultaneously advance. Upon release of the arm 32, the spring 54 urges the arm 32 to move in a rearwardly direction away from the handle 30; however, frictional engagement of the plungers 36, 38 with the two pairs of holes in the body 28 tend to resist rearward movement of the plungers 36, 38, such that the pawl 50 swings in clockwise direction viewing FIGS. 1 and 2 against the pressure of the spring 52, and enables the chisel-shaped lower front edge to ride over the top of the teeth 40 as the arm 32 moves rearwardly.

A rear, upper end of the pawl 50 extends through a hole in the body 28. When it is desired to move the plungers 36, 38 in a rearwardly direction, such as in instances where the cartridge 24 has been emptied, the user may depress the rear end of the pawl 50 to swing the front edge of the pawl 50 upwardly and disengage the teeth 40. While the pawl 50 is depressed in this manner, the user can grasp block 42 to pull the plungers 36, 38 in a rearwardly direction away from the cartridge 24.

Turning now to the cartridge 24, the cartridge 24 includes a first or upper cylindrical container 56 and a second or lower cylindrical container 58. Both of the containers 56, 58 have an elongated, cylindrical inner chamber 60 with a rear circular opening. The containers 56, 58 (including the longitudinal axes of the chambers 60) lie in parallel, side-by-side and preferably spaced apart relation to each other. Both chambers 60 also have a "D" shaped front opening separated from each other by an inner wall and surrounded by a protruding cylindrical neck 64.

In use of the system 20, the handle 30 is gripped by the fingers of the user while the arm 32 contacts rear portions of the user's palm and an adjacent, opposing section of the user's thumb. As the arm 32 is moved toward the handle 30, the plungers 36, 38 advance and cause the heads 46 to push pistons 92 (FIG. 3) in the chambers 60 in a forwardly direction toward the neck 64. Pistons 92 are provided with O-rings 49 around the circumference of piston 92 and is in sealing conformance with the inner wall of chamber 60. As the pistons 92 advance, components of a dental material that are located in the chambers 60 are expelled from the cartridge 24 and directed through the exit conduit 78, wherein the static mixing element 86 combines the two components to form the uniformly mixed, homogeneous dental material that is then expelled from a front discharge opening of the cannula.

Figure 4:
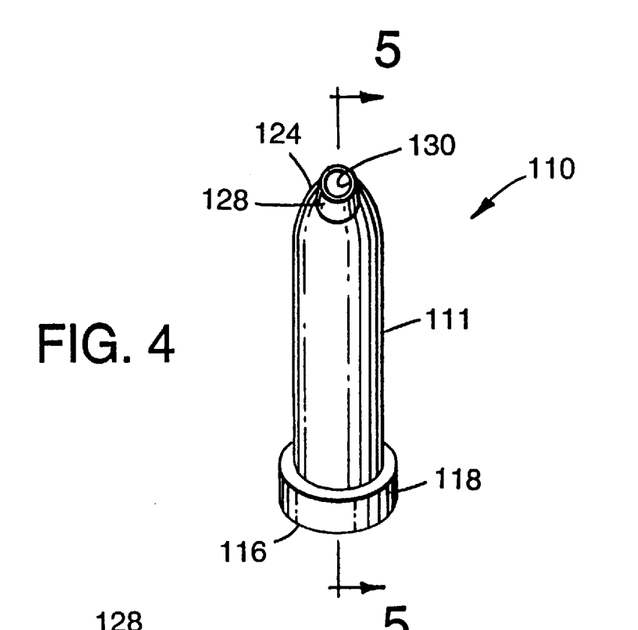
FIG. 4 is a perspective view of a cartridge of the invention.
Figure 5:
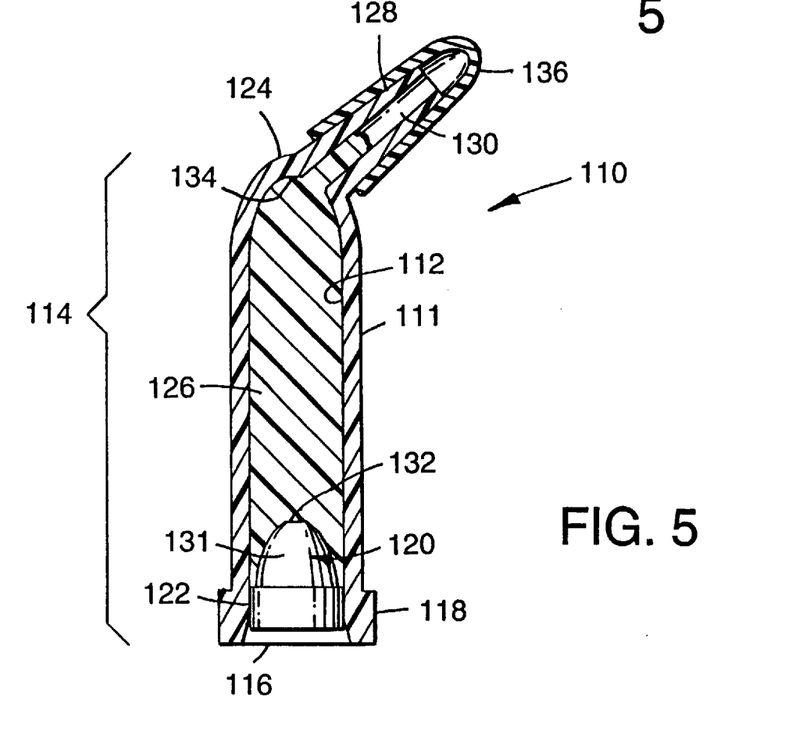
FIG. 5 is a sectional view of the embodiment of FIG. 4 along line 5—5, but including a cap over the discharge nipple.

FIGS. 4 and 5 illustrate embodiment 110 of a cartridge of the invention. Referring to FIG. 5, the illustrated embodiment 110 comprises generally cylindrical inner wall 112 defining elongate inner chamber 114. The body has open end 116 adapted by way of annular flange 118 to be detachably mounted in a hand-held ejector-type gun (not shown).

Displaceable piston 120 is inserted in open end 116. Sidewall 122 of piston 120 is in the form of a flange about the circumference of piston 120 and is in sealing conformance with inner wall 112. Piston 120 serves to seal the open end of the cartridge during storage in order to prevent exposure of enclosed non-aqueous paste dental material 126 to air. Piston 120 can be displaced toward discharge end 124 of body 110 by means such as a conventional handheld, manually powered, air powered, or motor powered ejector-type gun. When piston 120 is displaced toward discharge end 124, non-aqueous paste dental material 126 is expressed from discharge nipple 128, which extends from discharge end 124 and has orifice 130 through which the non-aqueous paste dental material is discharged. Piston 120 has bullet-shaped head 131 with a flattened end 132. The discharge orifice can be sealed with removable cap 136, which serves to seal the discharge end of the cartridge during storage.

The present invention will be further understood in view of the following examples which are merely illustrative and not meant to limit the scope of the invention.

EXAMPLE 1

The materials set out below in TABLE I were obtained from the indicated sources and select physical properties of importance for a cartridge material are set out in TABLE I. Tensile strength was measured using ASTM D638; 24 hour water absorption was measured using ASTM D570; and oxygen permeability was measured using ASTM D-3985 at 23° C./50% relative humidity ("RH"). Tensile strength of all the materials set out in TABLE I was suitable for a cartridge material; however, the 24 hour water absorption of nylon was too high along with its oxygen permeability being too low to be suitable material for a cartridge of the invention.

TABLE I

| Material | Tensile Strength (MPa) | Physical Property 24 Hour Water Absorption (%) | Oxygen Permeability (cm$^3$ mil/m$^2$ day atm) |
| --- | --- | --- | --- |
| Polyolefin[1] | 58 | 0.1 | 711 |
| Acetal[2] | 69 | 0.25 | 232 |
| Nylon[3] | 77 | 1.2 | 31 |
| Polypropylene[4] | 72 | 0.01 | 2320 |
| Polycarbonate[5] | 62 | 0.25 | 300 |

[1]Amorphous polyolefin; Zeonex 450 from Nippon Zeon Co., Ltd., Tokyo, Japan.
[2]Acetal; Delrin 107 from E. I. duPont de Nemours & Co., Wilmington, DE.
[3]Nylon: Zytel 101 from duPont.
[4]Polypropylene; PPX20GF, 20% glass filled from Compounding Technology Inc., Corona, CA.
[5]Polycarbonate; Miles 2558 from Bayer Corporation, Pittsburgh, PA.

Cartridges of the invention were independently injection molded using the materials set out in TABLE I except that Zeonex 250 (from Nippon Zeon Co., Ltd., Tokyo, Japan) was used instead of Zeonex 450 resin. The burst value of the cartridges was determined using the following procedure.

About one-half of the inner chamber of the cartridge was then filled with uncured Z100 restorative and a piston placed in the open end of the cartridge. Cartridges were then placed in low humidity (12%) for two weeks, cartridges were removed from the humitity chamber and the discharge end of each cartridge was plugged by forcing a small amount of 3M™ Restorative Z100 ("Z100"; from 3M) in the nipple end of the cartridge. The restorative at the tip was light cured with a 3M™ Visilux™ 2 visible light curing unit (from 3M) for about 100 seconds.

The cartridge was then placed in an Instron Model 1123 tensile testing machine operated at a crosshead speed of 2.0 mm/min. The piston was displaced by the tensile testing machine toward the discharge end until the cartridge failed by bursting. The mass (in kg) required to cause the cartridge to burst was measured and the average of five independent determinations was recorded. These values are set out below in TABLE II and show that all the materials except polypropylene had a sufficiently high burst value to be suitable materials from which to form a cartridge of the invention for storage of non-aqueous dental materials.

TABLE II

| Cartridge Material | Burst Value (kg) |
| --- | --- |
| Zeonex 250 | 44 |
| Delrin 107 | 51 |
| Zytel 101 | 40 |
| PPX20GF | 28 |
| Miles 2558 | 48 |

EXAMPLE 2

Eighty cartridges of the invention were independently injection molded from Zeonex 250 resin, Delrin 107, Zytel 101, Miles 2558 and PPX20GF. Each cartridge was sealed by capping the discharge nipple. Each molded and capped cartridge was then approximately two-thirds filled with Z100 restorative and a piston was placed in the open end of the cartridge. Each filled cartridge was then placed in a 5.1 cm square pouch made of a four layer laminated composite of polyester film, polyethylene film, aluminum foil and polyethylene film with an overall thickness of 0.02 cm (Rexam Medical Packaging, Mount Holly, N.J.). The edges of the pouch were heat sealed to form a hermetically sealed pouch.

The extrusion value of twenty cartridges of each material was measured immediately by removing each cartridge from its sealed pouch in a 25° C./ambient humidity environment. The cap was removed from the discharge nipple, the filled cartridge was placed in an Instron Model 1123 tensile testing machine and the restorative was extruded from the discharge end of the cartridge at a crosshead speed of 50 mm/min. The mass (in kg) required to extrude the restorative was measured and the average was recorded. In actual practice, the applied mass required to extrude the restorative is not constant throughout the process of extrusion. Rather, during extrusion a plateau is reached, and then the mass required remains relatively constant for the remainder of the extrusion process. For the purposes of the instant specification and claims, the extrusion value was taken to be the average applied mass observed for the time at which the plateau was reached until the end of the extrusion process.

The viscoelastic behavior of the restorative in each cartridge was determined by a consistency measurement. Consistency was measured as the spread of 1.04±0.01 g of restorative sandwiched between two 10.16×10.16 cm glass plates under a 907.2 g weight. The restorative was delivered onto the bottom plate, then the top plate and the 907.2 g weight were added. The combined mass of the top plate and the 907.2 g weight was 1027±10 g. After two minutes, the spread diameter of the restorative was measured to the nearest 0.8 mm, and two readings were averaged.

The remaining sixty cartridges were stored at 25° C./ambient humidity. At the time intervals set out in TABLE III, the aged cartridges were removed from the pouches and stored at 25° C./ambient humidity for about 4 hours. For each cartridge, the extrusion value was measured and the consistency determined as described above.

Set out below in TABLE III are the extrusion values and consistency measurements for each cartridge construction at the times indicated. A notation of "---" was used to indicate that no testing was performed at that time interval. The data in the table show the stability of a non-aqueous dental restorative in a cartridge of Zeonex material. Both the extrusion values and the consistency measurements of the restorative in a cartridge of Zeonex material are exhibited by the data in the table.

TABLE III

| Cartridge Material | Extrusion Values at Time Interval (Mo.) | | | | Consistency at Time Interval (Mo.) | | | |
|---|---|---|---|---|---|---|---|---|
| | Initial | 3 | 6 | 9 | Initial | 3 | 6 | 9 |
| Zeonex 250 | 8.78 | 9.83 | 10.25 | 10.72 | 35.3 | 35.6 | 35.1 | 35.5 |
| Delrin 107 | 9.16 | 12.35 | 15.69 | 17.28 | 35.0 | 33.8 | 32.7 | 32.5 |
| Zeonex 250 | 10.5 | — | — | — | 36.7 | — | — | — |
| Delrin 107 | 11.50 | 15.02 | — | — | 35.7 | 34.1 | — | — |
| Zytel 101 | 16.63 | 38.30 | — | — | — | — | — | — |
| Zeonex 250 | 9.10 | 9.87 | 9.75 | 11.16 | 34.9 | 34.9 | 35.2 | 34.9 |
| Delrin 107 | 8.10 | 10.31 | — | — | 35.7 | 34.1 | 33.8 | 31.8 |
| Miles 2558 | * | — | — | — | — | — | — | — |
| PPX20GF | * | — | — | — | — | — | — | — |

*Cartridge burst.

compartment of a IRµS™ FT-IR microanalysis system (from Spectra-Tech, Stamford, Conn.). An aperture of about 10×250 µm was used to collect spectral data, providing a line map (using the IRµS™ FT-IR software) of each shaving in 10 µm steps beginning at the inner surface of the cartridge (i.e., the first reading was the step from 0–10 µm). Each data point in TABLE IV was the ratio of the carbonyl absorbance for TEGDMA at 1720 cm$^{-1}$ to the absorbance for Zeonex, Zytel or Delrin at 1456 cm$^{-1}$, 1640 cm$^{-1}$ and 1470 cm$^{-1}$ respectively. The absorbance was measured using the peak height to a baseline determined by preselected points on the spectrum. A notation of "---" was used to indicate that the cartridge was not tested at that depth.

The data in TABLE IV show very low or no absorption of TEGDMA into the cartridge wall of Zeonex material with a significant amount of TEGDMA absorbed into the cartridge wall of the Delrin material up to a depth of 200 µm. The cartridge wall of Zytel material showed no TEGDMA; however, Zytel material is not a suitable cartridge material based on the 24 hour water absorption and oxygen permeability data provided in TABLE I.

The inventive capsules do not absorb TEGDMA to a depth deeper than 80 µm in a 10 day exposure evaluation. Preferably, the inventive cartridge do not absorb any volatile diluent material, and particularly the preferred volatile diluent materials, to a depth deeper than 80 µm in a 10 day exposure evaluation.

TABLE IV

| Cartridge Material | Depth into Cartridge Wall at 10 Days (µm) | | | | | | | |
|---|---|---|---|---|---|---|---|---|
| | 10 | 20 | 50 | 80 | 100 | 120 | 150 | 200 |
| Zeonex 250 | 0.0005 | 0.0003 | 0.0005 | 0.0000 | 0.0000 | — | — | — |
| Zeonex 450 | 0.0005 | 0.0007 | 0.0000 | 0.0000 | 0.0000 | — | — | — |
| Zytel 101 | 0.0000 | 0.0000 | 0.0000 | 0.0000 | 0.0000 | — | — | — |
| Delrin 107 | 0.38 | 0.33 | 0.28 | 0.24 | 0.19 | 0.08 | 0.03 | 0.01 |

EXAMPLE 3

TEGDMA Absorbtion

Cartridges of the invention were independently injection molded using Zeonex 450, Zeonex 250, Delrin 107 and Zytel 101 resins. The wall thickness of each cartridge was approximately 1200 µm. One molded cartridge of each material was sealed by capping the discharge nipple and filled with triethyleneglycol dimethacrylate ("TEGDMA"; from Sartomer). The TEGDMA filled cartridges were placed in a holder to maintain the cartridges in an upright position and stored in a chamber at 25° C./22% RH for 10 days.

On day 10, the cartridges were removed from the chamber and the caps were removed to allow the TEGDMA to drain from the cartridges. The cartridges were then rinsed with methanol and air dried. Each cartridge was cut in half and the cut areas were trimmed to obtain a relatively flat surface. Cross-sectional shavings about 8 µm thick of each cartridge were taken in a circular direction to avoid the possibility of smearing any residual material at the inner surface. A single shaving was either placed flat on one KBr crystal or mounted between two KBr crystals (if the sample curled). The KBr/shaving composite was then mounted in the sample Cartridges of the invention were independently injection molded using Zeonex 250 and Delrin 107 materials. Each cartridge was then sealed by capping the discharge nipple. Each molded and capped cartridge was approximately two-thirds filled with Z100 restorative and a piston was placed in the open end of the cartridge. Each filled cartridge was sealed in a foil pouch as described in EXAMPLE 2. The pouched cartridges were stored at 25° C./50% RH for 1 year for evaluation of the depth of penetration of TEGDMA into the cartridge material.

At 1 year, a cartridge was removed from its pouch and the Z100 restorative extruded from the cartridge. The empty cartridge was cut in half and any residual restorative observable under a light microscope was mechanically removed using a standard microscope tool without disturbing the inner surface of the cartridge. The sample was then prepared as described above for determination of depth of penetration of TEGDMA into the cartridge wall up to 400 µm. The data in TABLE V show the low absorption of TEGDMA into the wall of a cartridge made of Zeonex material compared to the absorption of TEGDMA into the wall of the cartridge made of Delrin material.

TABLE V

| Cartridge Material | Depth into Cartridge Wall at 1 Year ($\mu$m) | | | | | | | | | |
|---|---|---|---|---|---|---|---|---|---|---|
|  | 10 | 20 | 50 | 80 | 100 | 120 | 150 | 200 | 300 | 400 |
| Zeonex 250 | 0.07 | 0.02 | 0.01 | 0.008 | 0.001 | −0.008 | 0.012 | 0.000 | 0.000 | — |
| Delrin 107 | 0.48 | 0.45 | 0.45 | 0.36 | 0.36 | 0.43 | 0.49 | 0.43 | 0.31 | 0.02 |

What is claimed:

1. A cartridge comprising a cartridge body and paste for delivery of non-aqueous paste dental materials, said cartridge comprising
   a) a cartridge body made from an injection moldable material comprising a polymer selected from the group consisting of amorphous polyolefin polymers, said cartridge body having a 24 hour water absorption of less than 0.3%, a Burst Value of at least 30 kg, and an Oxygen Permeability greater than 180 cm$^3$ mil/m$^2$ day atm., said cartridge body comprising at least one chamber adapted for holding a non-aqueous paste dental material and simultaneously dispensing same; and
   b) a polymerizable non-aqueous paste dental material comprising a volatile diluent contained within said chamber of said cartridge body; wherein said cartridge is specially adapted to be mounted in a hand-held ejector-type gun, and further wherein said cartridge contains only non-aqueous materials.

2. The cartridge of claim 1, wherein said non-aqueous paste dental material is a dental restorative composition.

3. The cartridge of claim 1, wherein said amorphous polyolefin polymer is an amorphous polyethylene polymer.

4. The cartridge of claim 1, wherein said cartridge body has a Burst Value of greater than about 40 kg.

5. The cartridge of claim 1, wherein said cartridge body has a Burst Value of greater than about 50 kg.

6. The cartridge of claim 1, wherein said cartridge body has an Oxygen Permeability greater than 350 cm$^3$ mil/m$^2$ day atm.

7. The cartridge of claim 1, wherein said cartridge body has an Oxygen Permeability greater than 700 cm$^3$ mil/m$^2$ day atm.

8. The cartridge of claim 1, wherein said cartridge body has a Water Absorption of less than 0.2%.

9. The cartridge of claim 1, wherein said cartridge body has a has a Water Absorption of less than 0.1%.

10. The cartridge of claim 1, wherein said volatile diluent is selected from the group consisting of hydroxyethyl methacrylate, ethylene glycol dimethacrylate, triethylene glycol dimethacrylate, tetraethylene glycol dimethacrylate, polyethylene glycol (200) dimethacrylate, polyethylene glycol (400) diacrylate, polyethylene glycol (400) dimethacrylate, and diethylene glycol diacrylate.

11. The cartridge of claim 1, wherein said volatile diluent is selected from the group consisting of hydroxyethyl methacrylate and triethylene glycol dimethacrylate.

12. The cartridge of claim 1, wherein said paste has a consistency after extrusion from the cartridge of about 29 mm to 37 mm.

13. The cartridge of claim 1, wherein said paste has a consistency after extrusion from the cartridge of about 31 mm to 36 mm.

14. The cartridge of claim 1, wherein said paste has a consistency after extrusion from the cartridge of about 33 mm to 35 mm.

15. The cartridge of claim 1, being provided in a hermetically sealed foil pouch.

16. The cartridge of claim 1, wherein said cartridge body does not absorb TEGDMA to a depth deeper than 80 $\mu$m in a 10 day exposure evaluation.

* * * * *

UNITED STATES PATENT AND TRADEMARK OFFICE
CERTIFICATE OF CORRECTION

PATENT NO.: 5,848,894
DATED: December 15, 1998
INVENTOR(S): Ralph F. Rogers It is certified that error appears in the above-identified patent and that said Letters Patent is hereby corrected as shown below:

Claim 9, Column 12, line 16, delete the second occurrence of "has a".

Signed and Sealed this

Tenth Day of April, 2001

Attest:

NICHOLAS P. GODICI

*Attesting Officer*    *Acting Director of the United States Patent and Trademark Office*